United States Patent [19]

Hatton et al.

[11] Patent Number: 4,947,128

[45] Date of Patent: Aug. 7, 1990

[54] CO-VARIANCE MICROWAVE WATER CUT MONITORING MEANS AND METHOD

[75] Inventors: Gregory J. Hatton; David A. Helms; Michael G. Durrett; John D. Marrelli, all of Houston; Joseph D. Stafford, Bellaire, all of Tex.

[73] Assignee: Texaco IJN Inc, White Plains, N.Y.

[21] Appl. No.: 314,338

[22] Filed: Feb. 23, 1989

[51] Int. Cl.$^5$ ............................................. G01R 27/32
[52] U.S. Cl. ................................. 324/640; 73/61.1 R; 324/643
[58] Field of Search ..................... 324/58.5 A, 58.5 B, 324/58.5 R, 58 A, 58 B, 58 R, 637, 639, 642, 643, 640; 73/61.1 R; 340/603

[56] References Cited

U.S. PATENT DOCUMENTS

| | | | |
|---|---|---|---|
| 3,265,967 | 8/1966 | Heald | 324/58.5 A |
| 4,499,418 | 2/1985 | Helms et al. | 324/58.5 A |
| 4,764,718 | 8/1988 | Revus et al. | 324/58.5 A |

Primary Examiner—Reinhard J. Eisenzopf
Assistant Examiner—Robert W. Mueller
Attorney, Agent, or Firm—Robert A. Kulason; James J. O'Loughlin; Ronald G. Gillespie

[57] ABSTRACT

A co-variance microwave water cut monitor includes a test cell having a petroleum stress flowing through it while permitting the microwave energy to enter the test cell. A microwave source provides microwave energy to a circulator which in turn provides the microwave energy to an antenna. The antenna provides the petroleum stream in the test cell with the microwave energy and receives reflected microwave energy back from the stream. The reflected microwave energy is provided by the antenna to the circulator which in turn provides the reflected microwave energy as test microwave energy. A detector assembly connected to the circulator detects the intensity of the test microwave energy and provides a corresponding intensity signal. Indicator apparatus connected to the circulator to the microwave source and to the detector assembly provides an indication of the water cut of the petroleum stream in accordance with the intensity signal and the phase difference between the source provided microwave energy and the test microwave energy.

10 Claims, 1 Drawing Sheet

U.S. Patent        Aug. 7, 1990        4,947,128
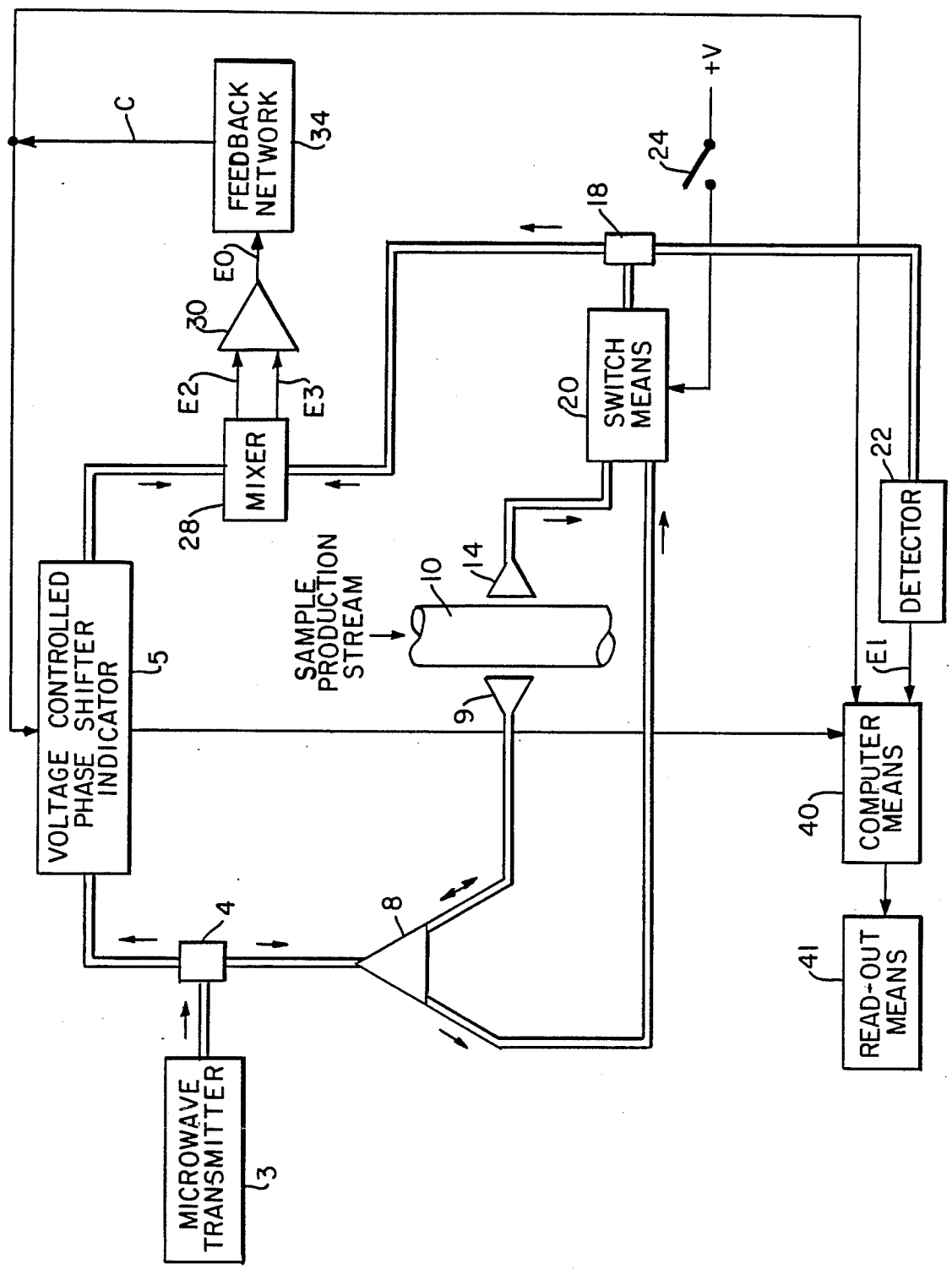

CO-VARIANCE MICROWAVE WATER CUT MONITORING MEANS AND METHOD

BACKGROUND OF THE INVENTION

Field of the Invention

The present invention relates to microwave means and methods of monitoring the water cut of a petroleum stream.

SUMMARY OF THE INVENTION

A co-variance microwave water cut monitor includes a test cell having a petroleum stream flowing through it while permitting the microwave energy to enter the test cell. A microwave source provides microwave energy to a circulator which in turn provides the microwave energy to an antenna. The antenna provides the petroleum stream in the test cell with the microwave energy and receives reflected microwave energy back from the stream. The reflected microwave energy is provided by the antenna to the circulator which in turn provides the reflected microwave energy as test microwave energy. A detector assembly connected to the circulator detects the intensity of the test microwave energy and provides a corresponding intensity signal. Indicator apparatus connected to the circulator to the microwave source and to the detector assembly provides an indication of the water cut of the petroleum stream in accordance with the intensity signal and the phase difference between the source provided microwave energy and the test microwave energy.

In another embodiment there is a second antenna which receives microwave energy that has passed through the petroleum stream and provides the received microwave energy as the test microwave energy. The detector assembly is connected to the second antenna and again provides an intensity signal corresponding to the intensity of the test microwave energy. Similarly the indicator apparatus is also connected to the second antenna instead of the circulator and provides the indication of the water cut of the petroleum stream in accordance with the intensity signal and the phase difference between the source provided microwave energy and the test microwave energy.

The objects and advantages of the invention will appear more fully hereinafter, from a consideration of the detailed description which follows, taken together with the accompanying drawings wherein two embodiments are illustrated by way of example. It is to be expressly understood, however, that the drawings are for illustrative purposes only and are not to be construed as defining the limits of the invention.

DESCRIPTION OF THE DRAWING

The drawing is a partial simplified block diagram of a microwave water cut monitor constructed in accordance with the present invention.

DESCRIPTION OF THE INVENTION

The water cut monitor shown in FIG. 1 includes a microwave source 3 providing electromagnetic energy, hereinafter referred to as microwave energy, at a microwave frequency. Source 3 is low powered and may use a microwave gun source. Source 3 provides microwave energy to directional coupler 4. Directional coupler 4 provides microwave energy to a conventional type voltage controlled phase shifter 5 and to a circulator 8. All conductance or carrying of microwave energy is accomplished by using conventional type waveguides and coaxial cable.

Circulator 8 provides microwave energy to an antenna 9. Antenna 9 transmits or radiates the microwave energy through a sample stream of a fluid mixture passing through a test cell 10. Test cell 10 may be a portion of a pipeline with "windows" made of material which permits passage of the microwave energy or it may be a portion of the pipeline made of the "window" material. The transmitted microwave energy passes through the fluid mixture and is received by an antenna 14 which provides the received microwave energy to a switch means 20 which in turn provides test microwave energy to a directional coupler 18, as hereinafter explained. Directional coupler 18 provides the test microwave energy to a detector 22 and to a mixer 28. Detector 22 provides a signal E1 corresponding to the intensity of the microwave energy received by antenna 14.

The fluid mixture also reflects some of the microwave energy back to antenna 9 which passes back through antenna 9 to circulator 8. Circulator 8 blocks the reflected microwave energy from feeding back to source 3 and provides the reflected microwave energy to switch means 20. Reflected microwave energy becomes more important as the distance between antennas 9 and 14 increases. This is especially true where a large pipeline carrying the fluid mixture is being monitored.

A positive direct current voltage +V is provided to a switch means 24 which is connected to switch means 20. With switch means 24 open, switch means 20 provides microwave energy from antenna 14 as test microwave energy. When switch 24 is closed, the reflected microwave energy from circulator 8 is provided by switch means 20 as the test microwave energy.

The microwave energy from voltage control phase shifter 5, hereinafter called the reference microwave energy, and the test microwave energy from directional coupler 22, are provided to a mixer 28 which mixes them to provide two electrical signals E2, E3, representative of the phases of the reference microwave energy and the test microwave energy, respectively.

A differential amplifier 30 provides an output signal E0 in accordance with the difference between signals E2 and E3. Signal E0 is a function of the phase difference between the reference microwave energy and the test microwave energy and is provided to a feedback network 34. Feedback network 34 provides a signal C to voltage control phase shifter 5, controlling the phase of the reference microwave energy, and to a mini-computer means 40. Signal E0, and hence the signal C, decreases in amplitude until there is substantially 90 phase difference between the reference microwave energy and the test microwave energy. Voltage control phase shifter 5 indicates the amount of phase shift required to eliminate the phase difference.

Signals E1 and C are provided to mini-computer means 40 which contains within it memory means having data related to phase and amplitude for various percentages of water cuts that could be encountered in the production stream. Phase Shifter 5 also provides an enabling signal to computer means 40 allowing computer means 40 to utilize signals C and E1 to select the proper water cut value computer means 40 provides signals, corresponding to the selected water cut value, to readout means 44 which may be either digital display means or record means or a combination of the two.

What is claimed is:

1. A petroleum stream microwave watercut monitor comprising:
   test cell means for having a petroleum stream flowing through it while permitting microwave energy to enter the test cell means,
   source means for providing microwave energy,
   antenna means for providing the petroleum stream flowing in the test cell means with microwave energy and for receiving reflected microwave energy back from the stream in the test cell means,
   circulating means connected to the source means and to the antenna means for providing the microwave energy from the source means to the antenna means and for providing reflected microwave energy from the antenna means as test microwave energy,
   detector means connected to the circulating means for the detecting the intensity of the test microwave energy and providing an intensity signal corresponding thereto, and
   indicator means connected to the source means and to the detector means for providing an indication of the watercut of the petroleum stream in accordance with the intensity signal and the phase difference between the source provided microwave energy and the test microwave energy.

2. A monitor as described in claim 1 in which the indicator means further comprises:
   a voltage controlled phase shifter receiving the microwave energy from said source means for phase shifting the source provided microwave energy in accordance with a phase shift signal to provide a reference microwave energy and to provide an enabling signal when the phase shifting is completed, and
   phase shift signal means receiving the reference microwave energy and the test microwave energy for providing the phase shift signal to the phase shifter until there is substantially a 90 phase difference between the reference microwave energy and the test microwave energy at which time the phase shifter's indicated phase shift corresponds to the water cut of the petroleum stream.

3. A monitor as described in claim 2 in which the phase shift signal means includes:
   mixer means connected to the circulating means for mixing the reference microwave energy from the phase shifter with the test microwave energy from the circulating means to provide two signals representative of the phases of the reference microwave energy and the test microwave energy from the circulating means,
   a differential amplifier connected to the mixer means provides an output signal in accordance with the difference between the two signals from the mixer means, and
   a feedback network connected to the phase shifter and to the differential amplifier which provides the phase shift signal in accordance with the output signal.

4. A monitor as described in claim 3 in which the indicator means further includes:
   water cut means connected to the phase shifter, to the detector means and to the phase shift signal means and responsive to the enabling signal from the phase shifter for determining the water cut of the petroleum stream in accordance with the intensity signal and the phase shift, and providing water cut signals corresponding thereto.

5. A monitor as described in claim 4 in which the indicator means further includes:
   read-out connected to the water cut means for providing a read-out of the selected water-cut value in accordance with the water cut signals from the computer means.

6. A petroleum stream microwave watercut monitoring method comprising the steps of:
   providing microwave energy from a source,
   using antenna means to provide a petroleum stream with the microwave energy from the source,
   receiving reflected microwave energy back from the petroleum stream with the antenna means,
   using circulator means connected to the source and to the antenna to provide the microwave energy from the source means to the antenna means and to provide the reflected microwave energy from the antenna means as test microwave energy,
   detecting the intensity of the test microwave energy,
   providing an intensity signal corresponding to the detected intensity of the test microwave energy, and
   providing an indication of the watercut of the petroleum stream in accordance with the intensity signal and the phase difference between the source provided microwave energy and the test microwave energy.

7. A method as described in claim 6 in which the indicator step further comprises:
   phase shifting the source provided microwave energy in accordance with a phase shift signal to provide a reference microwave energy,
   providing an enabling signal when the phase shifting is completed, and
   providing the phase shift signal until there is substantially a 90° phase difference between the reference microwave energy and the test microwave energy.

8. A method as described in claim 7 in which the phase shift signal step includes:
   mixing the reference microwave energy with the test microwave energy to provide two signals representative of the phases of the reference microwave energy and the test microwave energy from the circulating means,
   providing an output signal in accordance with the difference between the two signals from the mixer step, and
   providing the phase shift signal in accordance with the output signal.

9. A method as described in claim 8 in which the indicator means further includes:
   determining the water cut of the petroleum stream in accordance with the intensity signal and the phase shift signal, and
   providing water cut signals corresponding to the determined water cut.

10. A monitor as described in claim 9 in which the indicator step further includes:
    providing a read-out of the selected water-cut value in accordance with the water cut signals.

* * * * *